(12) United States Patent
Cho et al.

(10) Patent No.: US 8,288,738 B2
(45) Date of Patent: Oct. 16, 2012

(54) SUBSTRATE FOR DETECTING SAMPLES, BIO-CHIP EMPLOYING THE SUBSTRATE, METHOD OF FABRICATING THE SUBSTRATE FOR DETECTING SAMPLES, AND APPARATUS FOR DETECTING BIO-MATERIAL

(75) Inventors: Seong-ho Cho, Gwacheon-si (KR); Dong-ho Lee, Seongnam-si (KR)

(73) Assignee: Samsung Electronics Co., Ltd., Yeoungtong-gu, Suwon-si, Gyeonggi-do (KR)

( * ) Notice: Subject to any disclaimer, the term of this patent is extended or adjusted under 35 U.S.C. 154(b) by 433 days.

(21) Appl. No.: 12/613,118

(22) Filed: Nov. 5, 2009

(65) Prior Publication Data

US 2010/0108865 A1 May 6, 2010

(30) Foreign Application Priority Data

Nov. 5, 2008 (KR) .................. 10-2008-0109465

(51) Int. Cl.
*G01N 21/76* (2006.01)
*G01T 1/10* (2006.01)

(52) U.S. Cl. ....... 250/458.1; 359/619; 422/52; 422/129; 430/321

(58) Field of Classification Search .............. 250/458.1; 359/619; 422/52, 129; 430/321
See application file for complete search history.

(56) References Cited

U.S. PATENT DOCUMENTS

| | | | |
|---|---|---|---|
| 2003/0012693 A1* | 1/2003 | Otillar et al. | 422/58 |
| 2003/0148401 A1 | 8/2003 | Agrawal et al. | |
| 2005/0130226 A1* | 6/2005 | Ahn et al. | 435/7.1 |
| 2010/0111762 A1* | 5/2010 | Cho | 422/52 |
| 2010/0291313 A1* | 11/2010 | Ling | 427/475 |

FOREIGN PATENT DOCUMENTS

| | | |
|---|---|---|
| JP | 2006-058044 A | 2/2006 |
| JP | 2008020412 A | 1/2008 |
| KR | 100593939 B1 | 6/2006 |
| KR | 100610639 B1 | 8/2006 |

* cited by examiner

*Primary Examiner* — David Porta
*Assistant Examiner* — Casey Bryant
(74) *Attorney, Agent, or Firm* — Leydig, Voit & Mayer, Ltd.

(57) ABSTRACT

A substrate for detecting samples includes; a body, and a plurality of micro lenses arranged on the body and configured for attachment to at least one sample, wherein the at least one sample emits fluorescent light, and wherein the plurality of micro lenses condense the fluorescent light emitted from the at least one sample via refraction.

38 Claims, 11 Drawing Sheets

SUBSTRATE FOR DETECTING SAMPLES, BIO-CHIP EMPLOYING THE SUBSTRATE, METHOD OF FABRICATING THE SUBSTRATE FOR DETECTING SAMPLES, AND APPARATUS FOR DETECTING BIO-MATERIAL

CROSS-REFERENCE TO RELATED APPLICATION

This application claims priority to Korean Patent Application No. 10-2008-0109465, filed on Nov. 5, 2008, and all the benefits accruing therefrom under 35 U.S.C. §119, the content of which in its entirety is herein incorporated by reference.

BACKGROUND

1. Field

The present general inventive concept relates to a substrate for detecting samples, a bio-chip employing the substrate, and a method of fabricating the substrate, and more particularly, to a substrate for detecting samples, which is used for spectroscopically detecting a sample, a bio-chip employing the substrate, and a method of fabricating the substrate.

2. Description of the Related Art

Typical bio-chips have a structure in which micro-sized cells are arranged on a substrate in a matrix shape, wherein each of the cells includes biogenic organic materials such as nucleotide or protein. Bio-materials fixed on the substrate of the bio-chip are typically probe bio-materials that operate as biological receptors of target bio-materials.

Bio-chips may detect the target bio-materials via several different methods, such as via a hybridization reaction of nucleotides or interaction between bio-materials such as antigen-antibody interaction. The bio-chips may be used to research functions of genes, to search for illness-related genes, to analyze gene expression, to analyze protein distribution by detecting the bio-materials such as nucleotide or protein having a specific sequence, or various other uses.

When present, interaction between the bio-materials may be detected using a fluorescence detection method. The fluorescence detection method is a spectroscopic method of detecting fluorescent images by irradiating predetermined excitation lights on fluorescent materials tagged on the bio-materials. The detection of the fluorescent images is made using an optical scanning apparatus such as a photo-multiplier tube ("PMT"), a charge-coupled device ("CCD") scanner or a complementary metal oxide semiconductor ("CMOS") Image sensor ("CIS") scanner.

Fluorescent light obtained by irradiating predetermined excitation light onto fluorescent material tagged on bio-materials are much weaker than the excitation light and are emitted non-directionally, and intensity of fluorescent light detected by a photodetector may therefore be very weak. In addition, since the bio-materials are highly concentrated on the substrate and the fluorescent light is emitted non-directionally, the detected fluorescent image may be blurred by the fluorescent light emitted from the material tagged on a neighboring bio-material. Therefore, reliability of the detection results may be degraded.

SUMMARY

The present general inventive concept provides a substrate for detecting samples that may improve an efficiency of detecting fluorescent light emitted from samples such as bio-materials, a bio-chip including the substrate, a method of fabricating the substrate, and a bio-material detecting apparatus.

Additional aspects will be set forth in part in the description which follows and, in part, will be apparent from the description, or may be learned by practice of the invention.

According to an aspect of the present general inventive concept, a substrate for detecting samples includes; a body, and a plurality of micro lenses arranged on the body and configured for attachment to at least one sample, wherein the at least one sample emits fluorescent light, and wherein the plurality of micro lenses condense the fluorescent lights emitted from the at least one sample via refraction.

In one embodiment, a body of the substrate may be formed of a glass, a semiconductor, a dielectric material, a metal material, a polymer or a combination thereof.

In one embodiment, the plurality of micro lenses may be formed of an inorganic material, an organic material, a dielectric material, a polymer or a combination thereof.

In one embodiment, surfaces of the plurality of micro lenses may be surface treated so that the at least one sample may be attached to the surfaces of the micro lenses. In one embodiment, the surfaces of the plurality of micro lenses may be hydrophilic, and regions surrounding each of the plurality of micro lenses may be hydrophobic.

In one embodiment, the body may be formed of a hydrophobic material, and the plurality of micro lenses may be formed of a hydrophilic material.

In one embodiment, the plurality of micro lenses may have at least one of a convex, concave, and flat-hemispherical shapes.

In one embodiment, the substrate may further include; a plurality of anti-reflection layers formed on the surfaces of the plurality of micro lenses to transmit the fluorescent light emitted from the at least one sample. In one embodiment, the anti-reflection layers may be hydrophilic.

In one embodiment, the substrate may further include; reflection layers disposed between the plurality of micro lenses and the body to reflect the fluorescent light emitted from the at least one sample.

In one embodiment, the substrate may further include; reflection layers formed on the surfaces of the plurality of micro lenses to reflect the fluorescent light emitted from the at least one sample.

According to an aspect of the present general inventive concept, a bio-chip includes; a substrate on which a plurality of micro lenses are arranged, and at least one bio-material which emits fluorescent light when excited by an excitation light, the at least one bio-material being disposed on the plurality of micro lenses, wherein the plurality of micro lenses condense fluorescent light emitted from the at least one bio-material via refraction.

In one embodiment, the bio-chip may further include; a photodetector disposed on a surface of the substrate which is substantially opposite to a surface where the plurality of micro lenses are arranged, and the plurality of micro lenses condense the fluorescent light onto the photodetector. In one embodiment, the photodetector and the substrate are integrally formed as a single, unitary and indivisible unit. In one embodiment, the pixels of the photodetector may correspond to the plurality of micro lenses in one of a one-to-one and a one-to-many manner.

In one embodiment, the bio-chip may further include; an excitation light absorption filter disposed between the substrate and the photodetector, wherein the excitation light absorption filter may transmit the fluorescent light and absorbs the excitation light.

According to an aspect of the present general inventive concept, a method of fabricating a substrate for detecting samples includes; applying a photoresist on the substrate, patterning the photoresist to form patterns corresponding to a plurality of micro lenses, forming a plurality of micro lenses on the substrate using the patterned photoresist, applying different materials to the plurality of micro lenses and a plurality of regions surrounding each of the plurality of micro lenses to adjust at least one of a hydrophilic property and a hydrophobic property of at least one of the plurality of micro lenses and the plurality of regions surrounding each of the plurality of micro lenses.

In one embodiment, the forming of the plurality of micro lenses may include; reflowing the patterned photoresist to deform the patterned photoresist into the plurality of micro lenses. In one embodiment, the substrate may have a hydrophobic property and the photoresist may have a hydrophilic property.

In one embodiment, the forming of the plurality of micro lenses may include; reflowing the patterned photoresist to deform the patterned photoresist into the plurality of micro lenses; and etching an entire upper surface of the substrate, on which the deformed photoresist is formed, to form the plurality of micro lenses. In one embodiment, the method may further include; treating the surfaces of the plurality of micro lenses so that the samples may be attached to the plurality of micro lenses.

In one embodiment, the patterning the photoresist includes; forming a dielectric material layer on the substrate before applying the photoresist on the substrate, and the forming of the plurality of micro lenses may includes; reflowing the patterned photoresist to deform the patterned photoresist into the plurality of micro lenses; and etching an upper surface of the substrate, on which the deformed photoresist is formed, to form the plurality of micro lenses using the dielectric material layer. In one embodiment, the substrate may have a hydrophobic property and the dielectric material layer may have a hydrophilic property.

According to an aspect of the present general inventive concept, a bio-material detecting apparatus includes; a bio-chip including at least one bio material which emits fluorescent light when excitation light is irradiated thereon, and a substrate including a plurality of micro lenses, to which the at least one bio-material is attached, wherein the plurality of micro lenses condense fluorescent light emitted from the at least one bio-material, and a photodetector positioned where the fluorescent light is condensed and which detects the fluorescent light.

In one embodiment, the photodetector may be disposed at a bottom surface side of the substrate, which is opposite to a surface where the plurality of micro lenses are arranged. In one embodiment, the photodetector may be disposed at the surface of the substrate on which the plurality of micro lenses are arranged.

In one embodiment, the photodetector may be an image sensor or a scanner including a photomultiplier tube ("PMT"), a charge coupled device ("CCD"), a complementary metal oxide semiconductor ("CMOS") image sensor ("CIS").

In one embodiment, the bio-material detecting apparatus may further include; an excitation light absorption filter disposed between the bio-chip and the photodetector, wherein the excitation light absorption filter transmits the fluorescent light and absorbs the excitation light.

BRIEF DESCRIPTION OF THE DRAWINGS

These and/or other aspects will become apparent and more readily appreciated from the following description of the embodiments, taken in conjunction with the accompanying drawings of which:

FIG. 13A through FIG. 3D are diagrams illustrating an exemplary embodiment of processes of fabricating a substrate for detecting samples;

DETAILED DESCRIPTION

Figure 1:
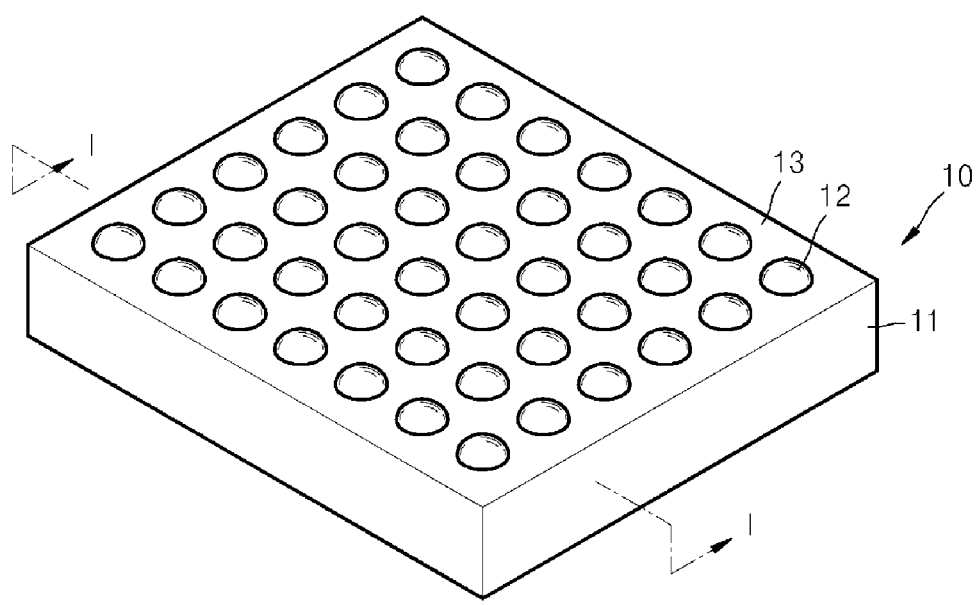
FIG. 1 is a schematic perspective view of an exemplary embodiment of a substrate for detecting samples.

The invention now will be described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower", can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments of the present invention are described herein with reference to cross section illustrations that are schematic illustrations of idealized embodiments of the present invention. As such, variations from the shapes of the illustrations as a result, for example, of manufacturing techniques and/or tolerances, are to be expected. Thus, embodiments of the present invention should not be construed as limited to the particular shapes of regions illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present invention.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

Hereinafter, the present invention will be described in detail with reference to the accompanying drawings.

Figure 2:
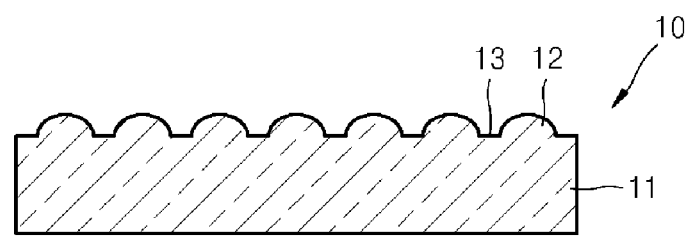
FIG. 2 is a cross-sectional view of the exemplary embodiment of a substrate taken along line I-I of FIG. 1.

FIGS. 1 and 2 schematically show an exemplary embodiment of a substrate for detecting samples.

Referring to FIGS. 1 and 2, the substrate 10 for detecting samples includes a plurality of micro lenses 12 on a surface thereof.

Samples attached on the substrate 10 of the present embodiment may be detected by a fluorescence detection method, for example, bio-materials such as nucleotides tagged by fluorescent materials may be detected due to fluorescence of the fluorescent materials.

In one exemplary embodiment, a body 11 of the substrate 10 and the micro lenses 12 may be formed of a glass, a semiconductor, a dielectric material, a polymer such as photoresist or other materials having similar characteristics. In one exemplary embodiment, the semiconductor may be II-VI, III-V, IV-IV compounds such as Si, GaAs, or InP, and the dielectric material may be nitride compounds or oxide compounds such as $SiO_x$, $Si_xN_y$, or $TiO_x$. The substrate 10 of the present embodiment is a transmissive substrate. That is, the body 11 is formed of a material that is transparent with respect to a wavelength band of the fluorescence so that the fluorescence emitted from the samples may be detected from a surface disposed substantially opposite to a surface to which the samples are attached.

The plurality of micro lenses 12 are formed in a predetermined arrangement, and samples such as the bio-materials are attached to the micro lenses 12. For example, in one exemplary embodiment when the substrate 10 is used as a DNA chip, the micro lens 12 becomes a minimum unit of a region, on which a plurality of probe nucleotides of the same kind are attached, and functions as a unit pixel of a fluorescent image that is obtained when excitation light is irradiated onto the DNA chip for detecting target nucleotides. Exemplary embodiments include configurations wherein the micro lens may have a diameter ranging from the sub-μm range to a few μm in size. In FIG. 1, a cross-sectional shape of the micro lens 12 is a circle, however, the cross-section of the micro lens 12 may be formed from other shapes, e.g., such as a polygon or a rectangle.

A surface of the micro lens 12 functions as a reaction region, to which samples are attached, and a peripheral portion 13 of the micro lens 12 functions as a non-reaction region, to which the samples are not attached. The surface of the micro lens 12 or the peripheral portion 13 of the micro lens 12 is treated so that the samples are attached only to the surface of the micro lens 12. For example, in one exemplary the samples or the liquid in which the samples are dispersed, the surface of the micro lens 12 may be treated to have an affinity to the samples or the liquid in which the samples are dispersed. The above surface treatment may vary depending on the samples that are to be detected. For example, in an exemplary embodiment wherein the substrate body 11 is formed of a hydrophobic material such as silicon, the micro lens 12 may be oxidized to have a hydrophilic property, although the surface treatment is not limited thereto. Various surface treatment methods, such as ion exchange surface treatments or immobilized metal surface treatments may be used according to the kind of samples to be analyzed.

The micro lens 12 has a refractive power to condense the fluorescent light emitted from the samples. The refractive power of the micro lens 12 is designed so that the fluorescent light may be condensed onto a photodetector, which will be described in more detail later.

Since the surface of the reaction region is convex, the surface area of the reaction region is greater than a plane surface area of equivalent size as viewed from a top plan view. Therefore, more samples may be attached to the convex area than those attached to the plane surface. In addition, the intensity of the fluorescent light emitted from the samples that are to be detected may increase, e.g., via refraction of light from the convex surface of the micro lens 12 through the substrate 10, thus concentrating the light at a point on a surface of the substrate substantially opposite to the surface on which the micro lens 12 is formed.

Figure 3:
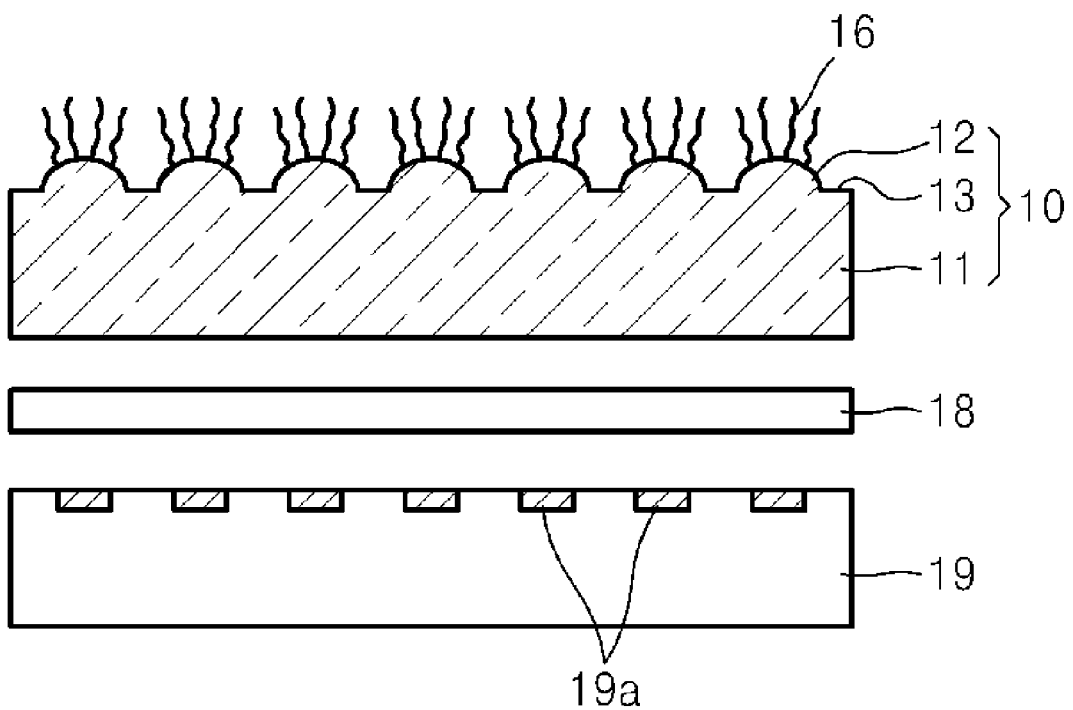
FIG. 3 is a diagram of an exemplary embodiment of a bio-chip including the substrate of FIG. 1.

FIG. 3 shows a bio-chip including the substrate for detecting samples shown in FIG. 1.

Referring to FIG. 3, the bio-chip includes the substrate 10, and probe bio-materials 16 attached on the substrate 10.

The probe bio-materials 16 may interact with target bio-materials that are to be detected, e.g., target bio-materials disposed in a sample fluid. The probe bio-materials are molecules that may perform interaction with the target bio-materials, for example, hybridization of nucleotides or an antigen-antibody interaction, for example, a nucleotide molecule having a sequence that is complementary to the nucleotide molecule that is to be detected. On the other hand, the target bio-materials may be biological organic materials such as enzyme of living creatures, protein, antibodies, nucleotides, microorganisms, cells and organs of animals and plants, nerve cells or various other similar materials.

In order to detect the target bio-materials, the integrated bio-chip of the present embodiment uses a fluorescence detection method. Therefore, fluorescent materials are tagged on the bio-materials. The tagged fluorescent materials may emit fluorescent light due to stimulation via an excitation light, or may be activated by the interaction between the probe bio-materials 16 and the target bio-materials to emit the fluorescent light due to the excitation light.

The surface of the substrate 10, on which the probe bio-materials 16 are attached, is treated as described above, and thus, the probe bio-materials 16 are attached only to the micro lenses 12 and not the surrounding portions of the substrate 10. In the present embodiment, the plurality of micro lenses 12 are disposed in a two-dimensional arrangement, e.g. a matrix shape. In one embodiment probe bio-materials of one type may be attached on one micro lens 12. In one embodiment, probe bio-materials 16 of different kinds may be attached to two different micro lenses 12. In one embodiment probe bio-materials 16 of the same kind may be attached to the plurality of micro lenses 12. In another embodiment, probe bio-materials of different types may be disposed on each of the micro lenses 12, respectively. The probe bio-materials 16 may be attached to the micro lenses 12 on predetermined locations through a semiconductor process, a bio-chemical process or other similar process.

Since the surface area of the micro lens 12, to which the probe bio-materials 16 are attached, is greater than a cross-sectional area of the micro lens 12, more probe-materials 16 may be attached to the bio-chip of the present embodiment than those attached to a hypothetical substrate having no micro lenses. That is, more probe-bio materials 16 may be attached to improve an efficiency of attaching bio-materials, e.g., the present embodiment provides a greater area for the attachment of a greater number of probe bio-materials 16 than a conventional substrate while maintaining substantially the same top plan profile (e.g., the same width and length). The more probe bio-materials 16 are attached to the substrate 10, the more the target bio-materials that interact with the probe bio-materials. Accordingly, the fluorescent light emitted from the samples also increases, and the efficiency of detecting the target bio-materials improves.

In of the embodiment wherein the substrate 10 is used in a DNA chip, probe nucleotides of a plurality of kinds are attached to predetermined micro lenses 12 in single stranded shapes, e.g., for hybridization, as the probe bio-materials 16. The probe nucleotides include the nucleotide having a sequence that is complementary to the sequence of the target nucleotide (for example, mRNA). When a liquid including the target nucleotides flows on the surface of the DNA chip, the probe nucleotides having the sequences that are complementary to those of the target nucleotides are combined with the target nucleotides via a hybridization reaction, and the nucleotides that are not combined with the probe nucleotides of the DNA chip are washed off, e.g., in a subsequent washing step. The nucleotide that is hybridized emits the fluorescent light due to the fluorescent material tagged thereon, and thus, it is determined whether the target nucleotide exists or not by detecting the location, from which the fluorescent light is emitted. Locations of the probe nucleotides, e.g., their location on the micro lenses 12, are determined in advance, and thus, existence of the plurality of target nucleotides may be determined from detected two-dimensional fluorescent images.

A photodetector 19 is attached to a bottom surface of the substrate 10 having the probe bio-materials 16 attached thereto. Embodiments of the photodetector 19 include an image sensor such as a photomultiplier tube ("PMT"), a charge coupled device ("CCD"), or a complementary metal oxide semiconductor ("CMOS") image sensor ("CIS"), a scanner using the image sensor or various other similar devices.

Embodiments of the photodetector 19 may include pixels 19*a* that correspond to the plurality of micro lenses 12 in a one-to-one manner or in one-to-many manner. That is, one or more pixels 19*a* of the photodetector 19 correspond to one micro lens 12. The micro-lens 12 condenses the fluorescent light emitted from the bio-materials attached thereon, e.g., by focusing the fluorescent light on a pixel of the photodetector 19 by refraction, and thus, cross-talk or noise caused by the fluorescent light emitted from the neighboring micro lens 12 may be prevented.

The fluorescent light is emitted due to excitation of the fluorescent material tagged on the target material by the excitation light, and since both the fluorescent light and the excitation light may be incident to the photodetector 19, the excitation light and the fluorescent light may be distinguished from each other. For example, in one embodiment an excitation light absorbing filter 18 may be disposed between the substrate 10 and the photodetector 19 to absorb the excitation light incident to the photodetector 19. The excitation absorbing filter 18 transmits the fluorescent light and absorbs the excitation light, and in one embodiment may be a wavelength selective filter that transmits the wavelength band of the fluorescent light which may be different from a wavelength band of the excitation light.

The bio-chip may be detachably attached to the excitation light absorbing filter 18 and the photodetector 19, or may be integrally coupled with the excitation light absorbing filter 18 and the photodetector 19; that is to say, the bio-chip may be formed as a single, unitary and indivisible member with the absorbing filter 18 and the photodetector 19. As described above, when the excitation light absorbing filter 18 and the photodetector 19 are detachably attached or integrally coupled to the bio-chip, a structure of a bio-material detecting apparatus that detects the bio-materials from the fluorescent image by irradiating the excitation light to the bio-chip may be minimized.

Figure 4:
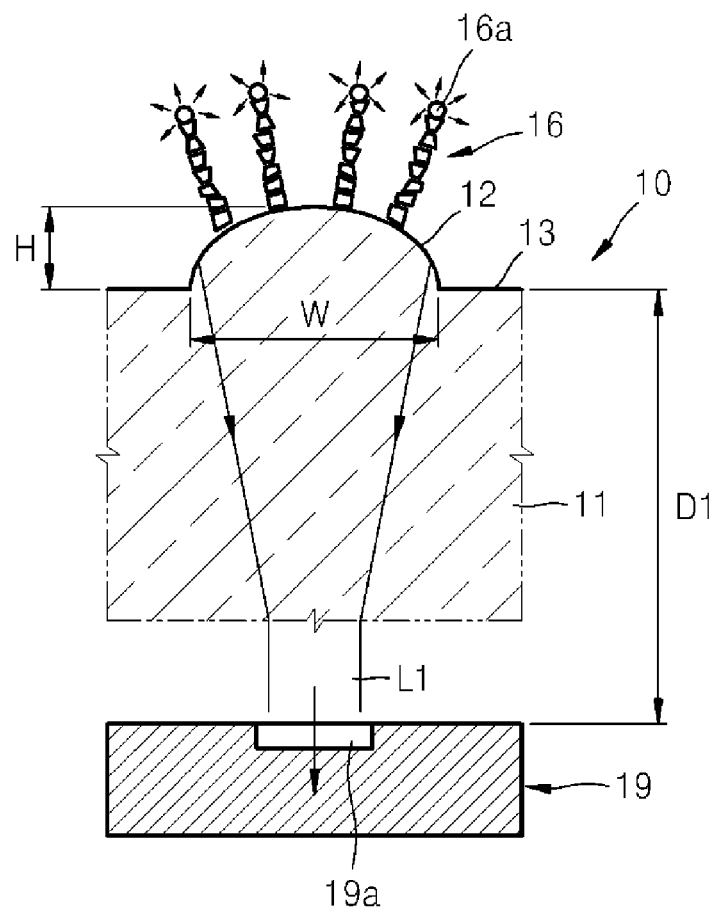
FIG. 4 is a diagram showing exemplary embodiments of optical paths of fluorescent light beams emitted from bio-materials attached on the exemplary embodiment of a bio-chip of FIG. 3.

FIG. 4 shows the interaction between the probe bio-materials and the target bio-materials to emit fluorescent light. In FIG. 4, reference numeral 16 denotes bio-materials obtained by combining the probe bio-materials and the target bio-materials. The fluorescent light emitted from the fluorescent materials 16a attached on bio-materials 16 is emitted non-directionally. Here, fluorescent light L1 proceeding toward the substrate 10 is condensed, e.g., focused, by the micro lens 12, and proceeds towards a bottom surface of the substrate 10. A cross-sectional area of a flux of the fluorescent light L1 that is condensed by the micro lens 12 is the smallest at a predetermined position at a distance D1 away from the surface of the body 11, and the cross-sectional area of the flux gradually increases away from the predetermined position at the distance D1. A Rayleigh length is defined as a length from a point where the cross-sectional area of the flux is the minimum to a point where the cross-sectional area of the flux becomes twice as large as at the minimum. Therefore, the photodetector 19 may be disposed at a position that is spaced apart from the micro lens 12 by about a Rayleigh length to improve the efficiency of detecting the fluorescent light. The pixels 19a of the photodetector 19 may correspond to the fluorescent light beams L1 that are condensed by the micro lenses 12 in a one-to-one manner or in a one-to-many manner. The position where the fluorescent light beam L1 has the smallest cross-sectional area may vary depending on the refractive power of the micro lens 12, and the refractive power of the micro lens 12 may be adjusted by adjusting a height H and a width W or a curvature of the micro lens 12. For example, in one embodiment when the photodetector 19 is attached to the bio-chip, the refractive power of the micro lens 12 is adjusted so that the position where the fluorescent light is condensed is around a bottom surface of the bio-chip.

Figure 5:
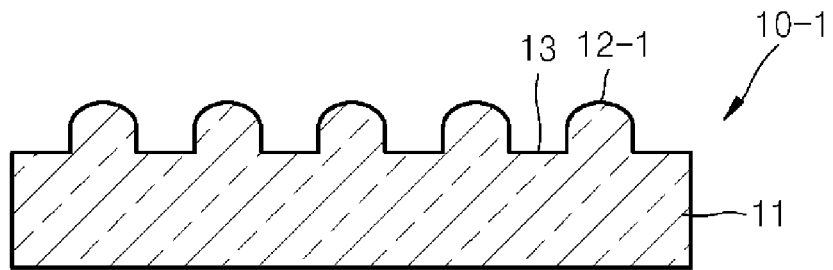
FIGS. 5 and 6 show modified exemplary embodiments of a micro lens formed on the exemplary embodiment of a substrate of FIG. 1.
Figure 6:
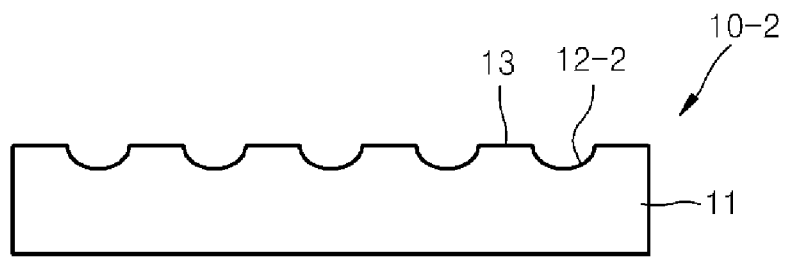

FIGS. 5 and 6 show modified embodiments of the micro lens formed on the substrate for detection samples of FIG. 1.

In the previous embodiment, the micro lens 12 was described as having a convex hemispherical shape, however, one or more embodiments are not limited to the above example. For example, in one embodiment as shown in FIG. 5, a substrate 10-1 for detecting samples may include micro lenses 12-1 having flat-hemispherical shapes, that is, hemispherical curves formed on end portions of cylinders.

FIG. 6 shows a substrate 10-2 for detecting samples, which has micro lenses formed as concave hemispherical shapes. In the previous embodiments, it is assumed that the refractive index of the substrate 10 (refer to FIG. 1) is greater than that of the outer portion, e.g., the micro lenses 12. However, the samples such as the target bio-materials are dispersed in liquid and the liquid flows along the surface of the substrate 10, and the refractive index of the liquid including the samples may be greater than that of the substrate 10. The substrate 10-2 of the present embodiment includes a plurality of micro lenses 12-2 having concave hemispherical shapes in the surface of the substrate body 11. When the refractive index of the liquid including the samples is relatively greater than that of the body 11, the fluorescent light may be condensed by the concave micro lenses 12-2.

Figure 7:
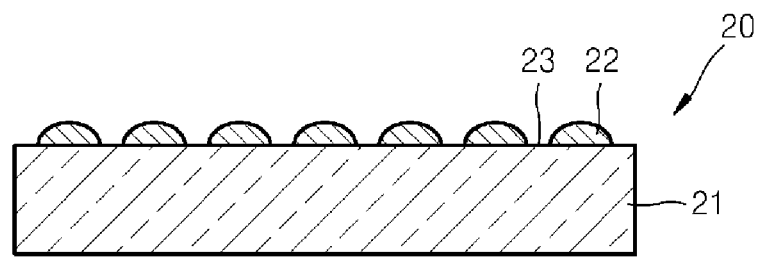
FIG. 7 is cross-sectional view of another exemplary embodiment of a substrate for detecting samples.

FIG. 7 is a cross-sectional view of another embodiment of a substrate for detecting samples.

Referring to FIG. 7, the substrate 20 includes a plurality of micro lenses 22 arranged on a substrate body 21. In the present embodiment, the components are substantially the same as those of the previous embodiment described with respect to FIGS. 1-3 except that the body 21 and the micro lenses 22 are formed of different materials from each other, and thus repeated detailed descriptions for the components are omitted.

Embodiments of the body 21 of the substrate may be formed of a glass, a semiconductor, a dielectric material, a polymer or other materials with similar characteristics. Embodiments of the micro lenses 22 may be formed of an inorganic material, an organic material, a polymer, a dielectric material or other materials with similar characteristics. The material for forming the micro lens 22 may be selected in consideration of the fabrication process. Since the substrate 20 is a transmissive substrate in the present embodiment, the body 21 and the micro lens 22 are formed of a material that is transparent with respect to a wavelength band of the fluorescent light.

A surface of the micro lens 22 becomes a reaction region, to which samples are attached, e.g., via hybridization, and a peripheral portion 23 of a top surface of the body 21 surrounding the micro lens 22 becomes a non-reaction region, to which the samples are not attached. The substrate body 21 is formed of a material that is not affinitive to the samples or the liquid in which the samples are dispersed, the surface of the micro lens 22 may be treated to have an affinity to the samples or the liquid in which the samples are dispersed. For example, in one embodiment when the substrate body 21 may be formed of a hydrophobic material such as silicon, the micro lens 22 may be formed of an oxide or a polymer having a hydrophilic property.

Figure 8:
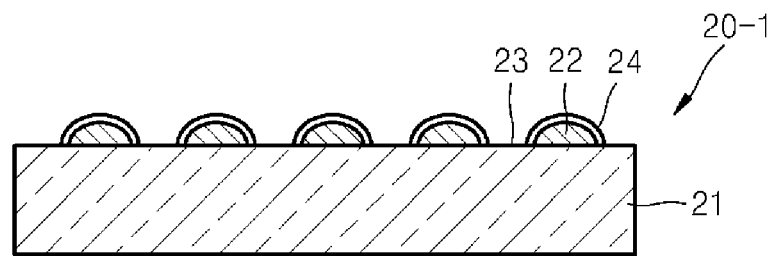
FIG. 8 is a diagram showing a modified exemplary embodiment of the substrate shown in FIG. 7.

FIG. 8 shows a modified embodiment of the substrate further including an anti-reflection surface. Referring to FIG. 8, a substrate 20-1 of the present modified embodiment further includes anti-reflection layers 24 formed on surfaces of the micro lenses 22. The anti-reflection layer 24 minimizes the loss of the fluorescent light that is emitted from the samples while the fluorescent light passes through the micro lens 22 and the body 21 of the substrate. Embodiments include configurations wherein the anti-reflection layer 24 may be formed of a material that is affinitive to the samples or the liquid including samples instead of performing the surface treatment of the micro lens 22. An additional anti-reflection layer (not shown) may be disposed on a boundary between the micro lenses 22 and the body 21.

Figure 9:
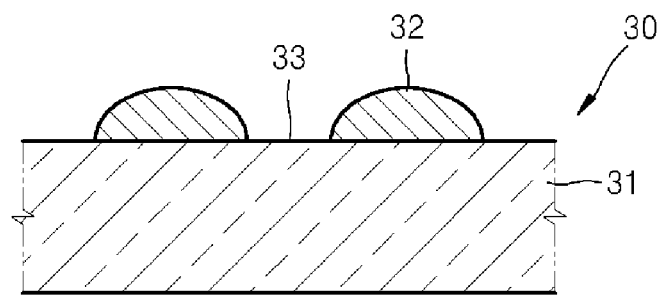
FIG. 9 is a cross-sectional view of another exemplary embodiment of a substrate for detecting samples.
Figure 10:
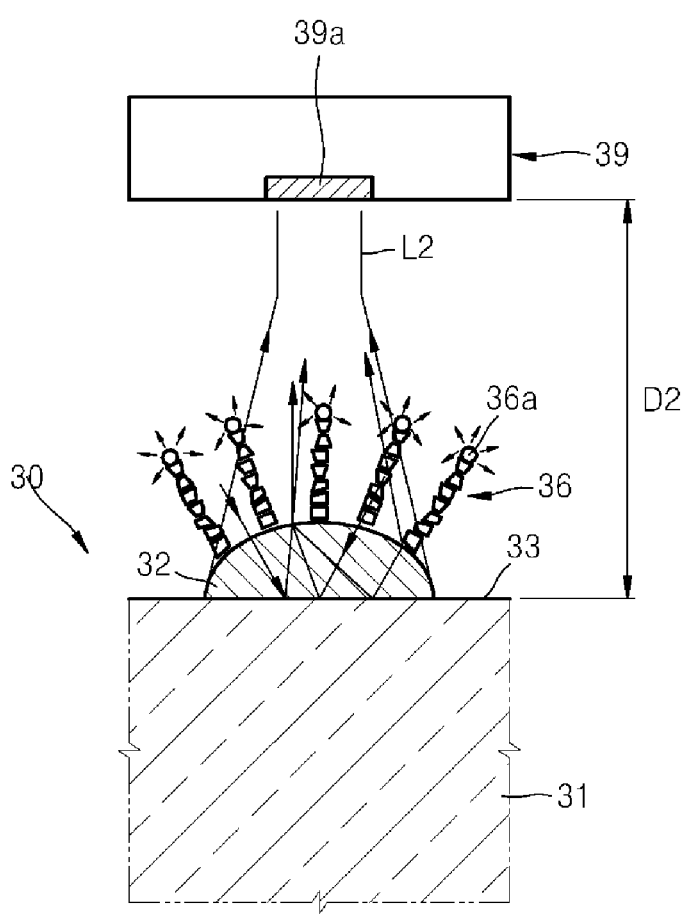
FIG. 10 is a diagram showing an exemplary embodiment of a bio-chip including the exemplary embodiment of a substrate of FIG. 9 and a photodetector.

FIG. 9 is a cross-sectional view of another embodiment of a substrate for detecting samples, and FIG. 10 shows an embodiment of a bio-chip including the substrate of FIG. 9 and a photodetector.

Referring to FIG. 9, the substrate 30 includes micro lenses 32 having refractive power to condense, e.g., focus, the fluorescent light emitted from the samples. The substrate 30 of the present embodiment is a reflective type substrate, unlike the above embodiments.

Embodiments of a body 31 of the substrate may be formed of a glass, a semiconductor, a dielectric material, a polymer or other similar material. Embodiments of the micro lens 32 may be formed of an inorganic material, an organic material, a polymer, a dielectric material or other similar material. A surface of the micro lens 32 functions as a reaction region, to which samples are attached, and a peripheral portion 33 of an upper surface of body 31 surrounding the micro lens 32 becomes a non-reaction region, to which the samples are not attached. In one embodiment the substrate body 31 is formed of a material that is not affinitive to the samples or the liquid in which the samples are dispersed, the surface of the micro lens 32 may be treated to have an affinity to the samples or the liquid in which the samples are dispersed. For example, in one embodiment when the substrate body 31 may be formed of a hydrophobic material such as silicon, the micro lens 32 may be formed of a polymer having a hydrophilic property.

Due to a difference between the refractive index of the material forming the micro lens 32 and the material forming the substrate body 31, some of the fluorescent light incident to the micro lens 32 may be reflected by an interface between the micro lens 32 and the body 31. The micro lens 32 is designed to condense the fluorescent light reflected from the interface between the micro lens 32 and the body 31 as will be described in more detail below with respect to FIG. 10.

Referring to FIG. 10, fluorescent light L2 emitted from fluorescent materials 36a attached on bio-materials 36 are non-directional. Some of the fluorescent lights L2 is emitted directly upward, or emitted downward and then proceeds upward by being reflected by the surface of the micro lenses 32 or by the interface between the micro lens 32 and the body 31. A photodetector 39 is oriented to face a surface of the substrate 30 on which the samples 36 such as the bio-materials are attached to detector the fluorescent light L2 proceeding upward. In one exemplary embodiment, the photodetector 39 is disposed above the micro lenses 32.

The micro lenses 32 are designed to condense, e.g., focus, the fluorescent light L2 reflected from the interface between the micro lenses 32 and the body 31 of the substrate 30. The condensed fluorescent light L2 has the minimum flux cross section at a predetermined distance D2 from the upper surface of the body 31, and the cross section of the flux increases at a distance less than the predetermined distance D2 away from the upper surface of the body 31. Therefore, the photodetector 39 may be disposed so that a focusing point of an image sensor or a scanner may be located at a position that is spaced apart from the upper surface of the body 31 at about a Rayleigh length (D2) from the upper surface of the body 31 in order to improve the efficiency of detecting the fluorescent light. Here, the pixels 39a of the photodetector 39 may correspond to the fluorescent light L2 condensed by the micro lens 32 in a one-to-one or in a one-to-many manner.

Figure 11:
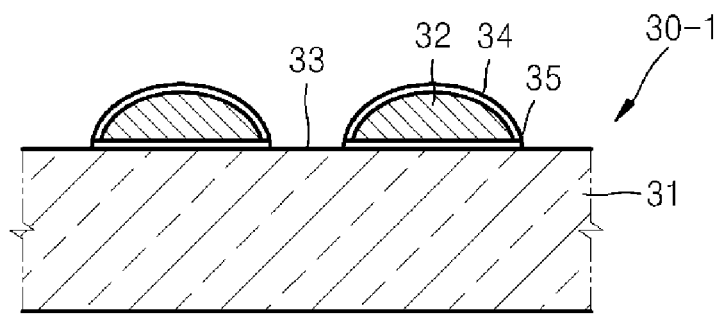
FIG. 11 is a cross-sectional view of another exemplary embodiment of a substrate for detecting samples.

FIG. 11 is a cross-sectional view of another embodiment of a substrate for detecting samples.

The substrate 30-1 includes the body 31, the micro lenses 32, an anti-reflection layer 34, and a reflection layer 35. The substrate 30-1 of the present embodiment is substantially the same as the embodiment of a substrate 30 shown in FIG. 9 except for that the anti-reflection layer 34 and the reflection layer 35 are additionally included.

The anti-reflection layer 34 formed on the surfaces of the micro lenses 32 to prevent the fluorescent light from being reflected by the surfaces of the micro lenses 32. The reflection layer 35 is disposed on the interface between the body 31 and the micro lens 32 to enhance the fluorescent light reflected on the interface between the body 31 and the micro lens 32. The anti-reflection layer 34 may be formed of a material that is affinitive to the samples or the liquid including the samples instead of performing the surface treatment of the micro lens 32. For example, in one embodiment the body 31 of the substrate may be formed of a hydrophobic material such as silicon, and the reflection layer 35 may be formed of a metal having a hydrophilic property.

Figure 12:
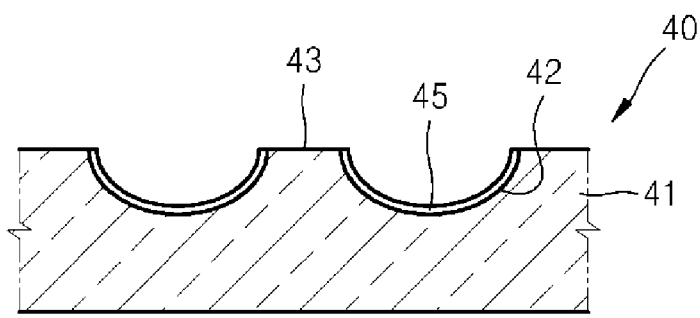
FIG. 12 is a cross-sectional view of another exemplary embodiment of a substrate for detecting samples.

FIG. 12 is a cross-sectional view of another embodiment of a substrate for detecting samples.

Referring to FIG. 12, a substrate 40 of the present embodiment includes a body 41, micro mirrors 42 formed as concave hemispheres in the body 41 of the substrate 40, and reflective layers 45 formed on the micro mirrors 42.

The body 41 of the substrate is formed of a material that is not affinitive to the samples or the liquid including samples, and the reflection layer 45 is formed of a material that is affinitive to the samples or the liquid including samples. For example, in one embodiment the body 41 of the substrate may be formed of a hydrophobic material such as silicon, and the reflection layer 45 may be formed of an oxide or a metal having a hydrophilic property.

Next, one or more embodiments of a method of fabricating the substrate for detecting samples will be described.

FIGS. 13A through 13D show processes of fabricating an embodiment of a substrate for detecting samples. In the present embodiment, a polymer such as photoresist is used as a micro lens.

Figure 13A:
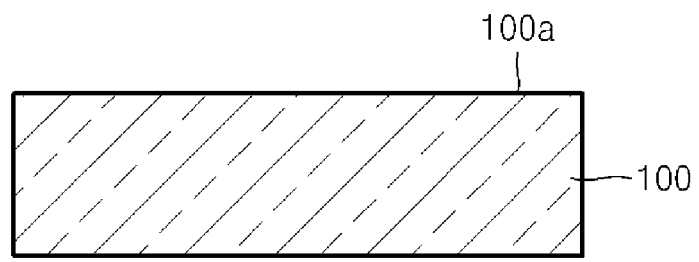

Referring to FIG. 13A, a substrate 100 is prepared. Embodiments of the substrate 100 may be formed of a glass material, a semiconductor material, a metal material, a dielectric material, a polymer or other materials having similar characteristics. The substrate 100 may be formed of a material that is not affinitive to samples or liquid in which the samples are dispersed. For example, in one embodiment the substrate 100 may be a silicon substrate having a hydrophobic property when the sample or liquid in which the sample is to be dispersed has a hydrophilic property. A surface of the substrate 100 may be formed as a planarized layer or may be planarized using a chemical mechanical polishing ("CMP") process or other planarizing process.

Figure 13B:
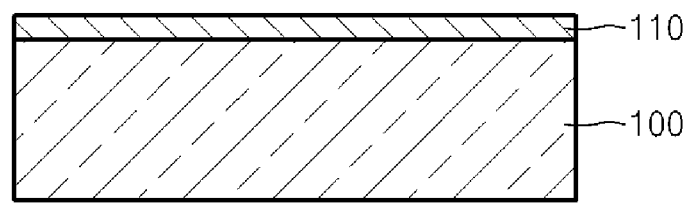

Referring to FIG. 13B, a photoresist 110 is applied onto the substrate 100. In the present embodiment the photoresist is a material that is transparent for the wavelength band of the fluorescent light emitted from the samples such as bio-materials.

Figure 13C:
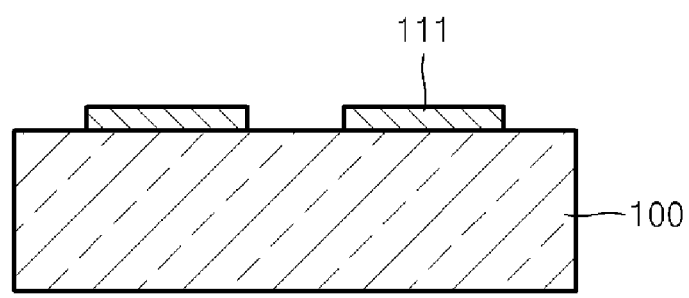

Next, as shown in FIG. 13C, patterns of a plurality of micro lenses are to be formed in the photoresist 110 using an etching process. Here, the patterned photoresists 111 have pillar shapes.

Figure 13D:
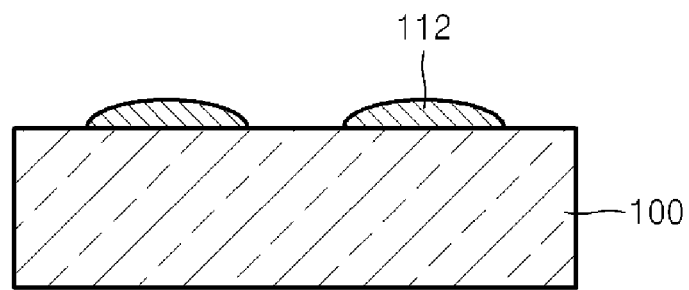

Next, as shown in FIG. 13D, the patterned photoresists 111 (refer to FIG. 13C) are deformed to form rounded photoresists 112. In one embodiment, for example, the patterned photoresists 111 are deformed using a reflow process. The reflow process is a process of applying heat of a temperature higher than a glass transition temperature (Tg) of the photoresist material, for example, a temperature of about 120° C.-200° C. to the patterned photoresist 111, and then, the patterned photoresists 111 are melted to have rounded surfaces. Here, a thickness and a width of the patterned photoresist 111 and the heating temperature and heating time in the reflow process may be adjusted to result in a curvature of the curved surface of the rounded photoresist 112. In the present embodiment, the rounded photoresists 112 are directly used as the micro lens structures.

Next, a process of applying an anti-reflection layer (refer to 24 of FIG. 8) onto the rounded photoresists 112 may be further performed.

According to the present embodiment, the hydrophilic and hydrophobic properties of the substrate and the photoresist may be selected appropriately, and thus, the hydrophilicity and the hydrophobicity of the regions where the micro lenses 112 are formed and the other regions may be controlled freely. The fabrication processes of the present embodiment are for fabricating the substrate for detecting the samples, however, alternative embodiments may apply semiconductor fabrication processes selectively to the substrate 100.

FIGS. 14A through 14E illustrate another embodiment of processes of fabricating a substrate for detecting samples.

Figure 14A:
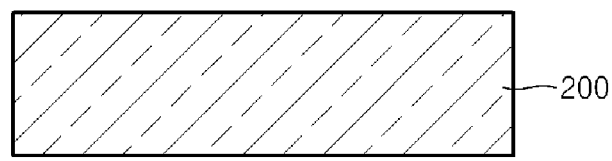
FIGS. 14A through 14E are diagrams illustrating another exemplary embodiment of processes of fabricating a substrate for detecting samples.

Referring to FIG. 14A, a substrate 200 is prepared. Embodiments of the substrate 200 may be formed of a glass material, a semiconductor material, a metal material, a dielectric material, a polymer or other materials having similar characteristics. The substrate 200 may be formed of a material that is not affinitive to samples or liquid in which the samples are dispersed. For example, in one embodiment the substrate 200 may be a silicon substrate having a hydrophobic property, similar to that described above with respect to FIG. 13A.

Figure 14B:
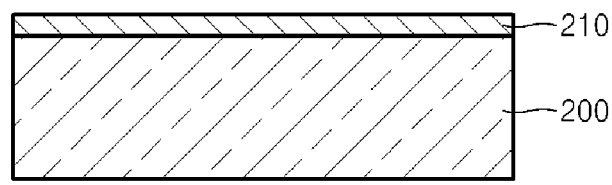
Figure 14C:
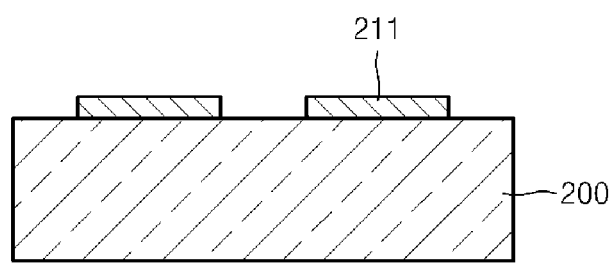

Referring to FIGS. 14B and 14C, a photoresist 210 is applied onto the substrate 200, and an etching process is performed to form patterns of a plurality of micro lenses in the photoresist 211. In this embodiment the patterned photoresists 211 are formed as pillars.

Figure 14D:
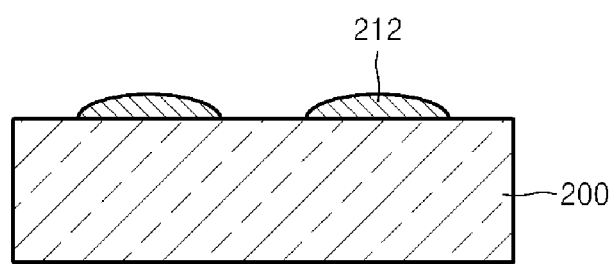

Next, as shown in FIG. 14D, the patterned photoresists (211 of FIG. 14C) having the pillar shapes are deformed to rounded photoresists 212, for example, using a reflow process. As described above, a thickness and a width of the patterned photoresist 211 and the heating temperature and heating time in the reflow process may be adjusted to adjust a curvature of the curved surface of the rounded photoresist 212.

Figure 14E:
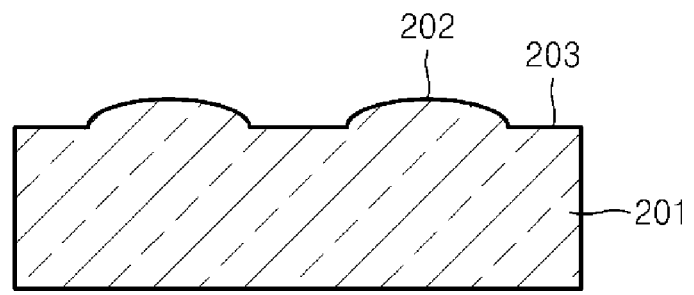

Next, as shown in FIG. 14E, an etch-back process is performed to etch the entire surface of the substrate 200 on which the rounded photoresists (212 of FIG. 14D) are formed. The surfaces on which the rounded photoresists 212 are not formed is evenly etched, however, the surfaces, on which the rounded photoresists 212 are formed, may be etched differently according to the thickness of the photoresists 212. Therefore, rounded micro lenses 202 corresponding to the rounded photoresists 212 are formed. That is, the micro lenses 202 are formed by etching the substrate 200 in the present embodiment, and therefore the micro lenses 202 and the substrate 200 are formed from the same material and are integral with one another, being formed as a single, unitary and indivisible member. For example, when the substrate 200 is a semiconductor substrate such as Si, GaAs, or InP, the micro lenses 202 may be semiconductor lenses.

Next, surfaces of the micro lenses 202 are treated so that the micro lenses 202 have the affinity to the samples or the liquid in which the samples are dispersed, or coated with an anti-reflection agent that is affinitive to the samples or the liquid in which the samples are dispersed. For example, when the silicon substrate is used, the portions forming the micro lenses 202 may be oxidized while the portions of the substrate 200 not corresponding to the micro lenses 202 are not oxidized.

FIGS. 15A through 15E illustrate another embodiment of processes of fabricating a substrate for detecting samples.

Figure 15A:
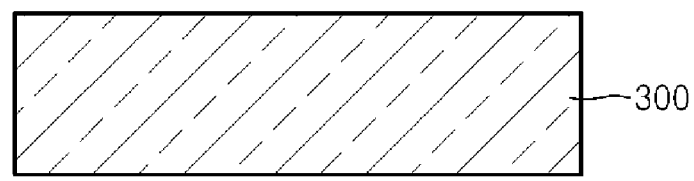
FIGS. 15A through 15E are diagrams illustrating another exemplary embodiment of processes of fabricating a substrate for detecting samples.

Referring to FIG. 15A, a substrate 300 is prepared. The substrate 300 may be formed of a material that is not affinitive to samples or liquid in which the samples are dispersed, as described in detail above.

Figure 15B:
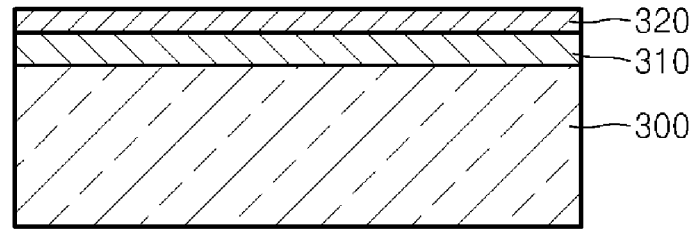

As shown in FIG. 15B, a dielectric material 310, embodiments of which include an oxide, and a photoresist 320 are sequentially applied on the substrate 300. Since the dielectric material 310 will be formed into micro lenses, the dielectric material 310 may be affinitive to the samples or the liquid in which the samples are dispersed.

Figure 15C:
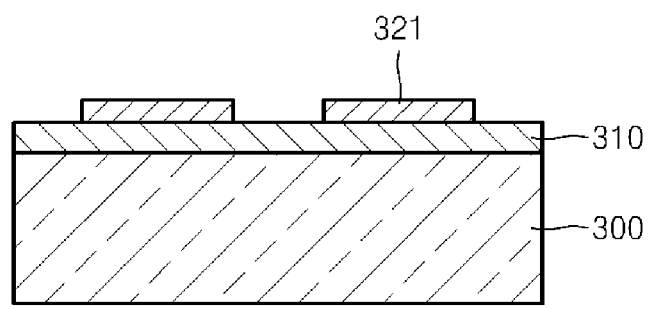

Next, as shown in FIG. 15C, patterns corresponding to a plurality of micro lenses are formed in the photoresist 321 using an etching process. The patterned photoresists 321 are formed as pillars.

Figure 15D:
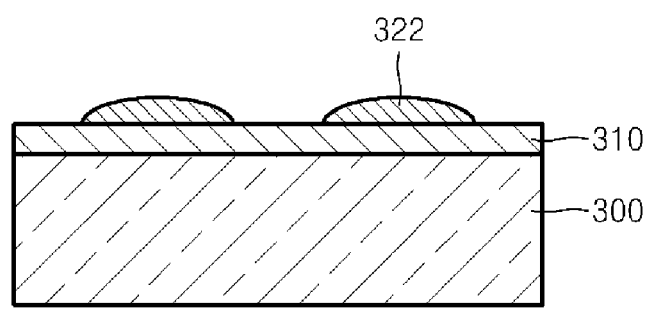

Next, as shown in FIG. 15D, the patterned photoresists (321 of FIG. 15C) having the pillar shapes are deformed to rounded photoresists 322, for example, using a reflow process as described in detail above. As described above, a thickness and a width of the patterned photoresist 321 and the heating temperature and heating time in the reflow process may be adjusted to adjust a curvature of the curved surface of the rounded photoresist 322.

Figure 15E:
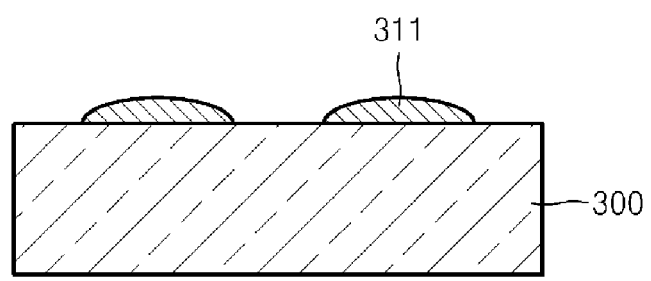

Next, as shown in FIG. 15E, an etch-back process is performed to etch the entire surface of the substrate 300, on which the rounded photoresists (322 of FIG. 15D) are formed. The dielectric material 310, on which the rounded photoresists 322 are not formed, is evenly etched, however, the dielectric material 310, on which the rounded photoresists 322 are formed, may be etched differently according to the thickness of the photoresists 322. Therefore, rounded micro lenses 311 corresponding to the rounded photoresists 322 are formed. That is, the micro lenses 311 are dielectric lenses formed of the dielectric material. The etching may or may not remove a portion of the substrate 300 depending upon an etching process and the desired shape of the dielectric material 310 remaining to form the micro lenses 311.

Next, a process of applying an anti-reflection layer (refer to 24 of FIG. 8) onto the rounded micro lenses 311 may be further performed.

According to the present embodiment, the hydrophilic and hydrophobic properties of the substrate and the dielectric material may be selected appropriately, and thus, the hydrophilicity and the hydrophobicity of the regions where the micro lenses are formed and the other regions may be controlled freely.

A bio-chip may be fabricated by attaching bio-materials on the substrate for detecting samples according to any of the previous embodiments. For example, embodiments include configurations wherein DNA bases such as adenine (A), guanine (G), cytosine (C), and thymine (T) are stacked on the different micro lenses in different sequences, and thus, a DNA chip having probe DNA molecules having predetermined sequences may be fabricated.

Figure 16:
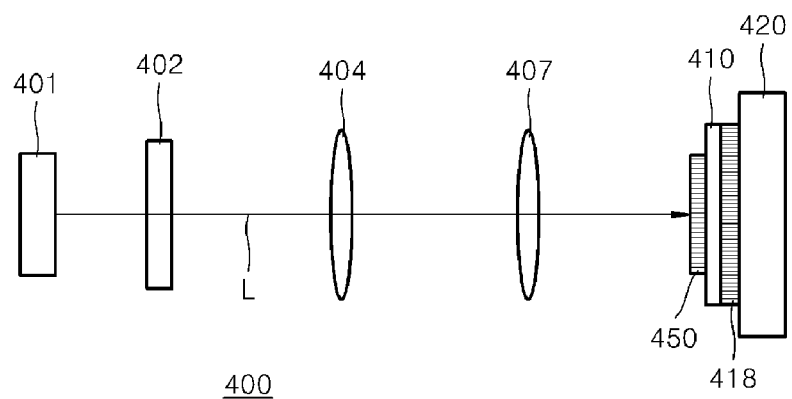
FIG. 16 is a schematic block diagram of an exemplary embodiment of a bio-material detecting apparatus.

FIG. 16 is a schematic block diagram of an embodiment of a bio-materials detecting apparatus.

Referring to FIG. 16, the transmissive type bio-materials detecting apparatus 400 includes a light source 401 that is an illuminating optical system irradiating excitation light to a bio-chip 450, a light diffusing device 402, a collimating lens 404, and a condensing lens 407. In addition, the bio-material detecting apparatus 400 further includes a system for detecting fluorescent light emitted from the bio chip 450 due to excitation thereof by the excitation light from the light source 401, the system including an excitation light absorbing filter 410, a photodetector 418, and a stage 420. While the present embodiment includes a stage 420 on which the integrated bio-chip 450 and the photodetector 418 are installed, alternative embodiments may omit the stage 420.

The bio-chip 450 included in the bio-material detecting apparatus 400 of the present embodiment is a transmissive type bio-chip, and may be any of the embodiments of the substrate for detecting samples described with reference to FIGS. 1 through 8.

The light source 401 emits excitation light L. The excitation light L is for exciting fluorescent materials attached on the bio-materials in the bio-chip 450. In one embodiment light having a wavelength of about 500 nm may be used as the excitation light L, however, the wavelength of the excitation light L may be varied according to the fluorescent materials tagged on the bio-materials.

The light diffusing device 402 diffuses the excitation light L evenly so that the excitation light L has an even intensity throughout the entire cross section thereof. For example, in one embodiment the light diffusing device 402 may be a bar type light integrator or a micro patterned substrate. The excitation light L has uniform intensity throughout the entire cross section thereof so that light with constant intensity is irradiated to either a particular region of, or the entire region of, the bio-chip 450.

The collimating lens 404 changes the excitation light L into parallel light. In FIG. 16, the collimating lens 404 is disposed between the light diffusing device 402 and the condensing lens 407, however, the collimating lens 402 may be disposed between the light source 401 and the light diffusing device 402. Moreover, in embodiments wherein the excitation light L emitted from the light source 201 does not significantly diverge and the condensing lens 407 may sufficiently condense the excitation light L, the collimating lens 404 may not be omitted.

The condensing lens 407 condenses the excitation light L so that a light spot having a predetermined diameter is formed on the bio-chip 450. The diameter of the light spot may cover a part of the bio-chip 450 or the entire region of the bio-chip 450. The purpose of the illuminating optical system is simply to provide an excitation light having a uniform intensity to the desired portion of the bio-chip 450 and any additional elements may be added to the system to accomplish this purpose. Similarly, elements may be omitted from the illuminating optical system as long as the general purpose is maintained.

The excitation light absorbing filter 410 and the photodetector 418 are disposed on a bottom surface of the bio-chip 450. In the present embodiment, the photodetector 418 detects the fluorescent light only and the excitation light has an intensity that is much stronger than that of the fluorescent light, and thus, if the excitation light is not removed from the light received by the photodetector 418, the excitation light may interfere with the precise light detection of the fluorescent light. In one embodiment the excitation light absorbing filter 410 only transmits the fluorescent light and absorbs the excitation light in order to detect only fluorescent light. In general, since the wavelength of the fluorescent light may be longer than that of the excitation light, a wavelength selective filter that transmits the wavelength band of the fluorescent light may be used as the excitation light absorbing filter 410.

The photodetector 418 detects the fluorescent light emitted from the bio-chip 450. The photodetector 418 may be, for example, an image sensor such as a PMT, a CCD, a CIS or other similar device as described above.

In the present embodiment, the excitation absorbing filter 410 and the photodetector 418 are integrally formed on the stage 420, and the bio-chip 450 is detachably attached on the excitation light absorbing filter 410. Here, the photodetector 418 may be disposed at a position where the fluorescent light is condensed to a minimum width by the refractive index of the micro lenses, or within a Rayleigh length from the above position. In the above structure, the photodetector 418 includes pixels corresponding to the micro lenses in a one-to-one or a one-to-many manner, and thus, the fluorescent light emitted from the bio-materials may be detected by the pixels in a one-to-one or a one-to-many manner.

When the light spot of the excitation light L covers the entire surface of the bio-chip 450, the photodetector 418 may simultaneously detect all of the fluorescent images emitted from the bio-chip 450. When the light spot of the excitation light L covers only a part of the bio-chip 450, the stage 420 or the illuminating optical system moves to cover the entire surface of the bio-chip 450 in a time-sequential manner. In addition, the 450 by combining the fluorescent images emitted from the bio-chip 450 in a time-sequential order.

The bio-chip 450 may be integrally coupled to the excitation light absorbing filter 410 and the photodetector 418, e.g., formed as a single, unitary and indivisible member. In such an embodiment, the excitation light absorbing filter 410 and the photodetector 418 may be omitted from the bio-material detecting apparatus. As described above, since the detecting optical system is configured with a simple structure, the bio-material detecting apparatus may be miniaturized.

Moreover, FIG. 16 shows that the photodetector 418 is disposed adjacent to the bottom surface of the bio-chip 450, however, the present embodiment is not limited to the above embodiment. The position where the cross-sectional area of the condensed fluorescent light becomes the smallest may be spaced apart from the bio chip 450 at various locations according to the refractive index or the curvature of the micro lenses. In such an embodiment, a photodetector including an additional scanning optical system that scans the fluorescent images and an image sensor such as PMT, CCD, and CIS may be used instead of the photodetector 418 that is adjacent to the bottom surface of the bio-chip 450.

Figure 17:
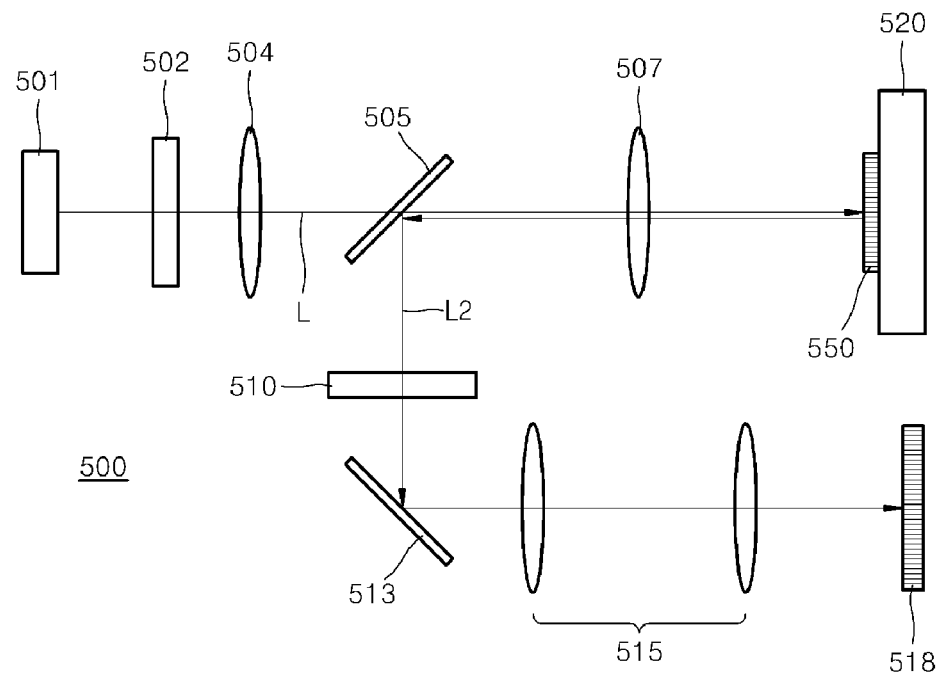
FIG. 17 is a schematic block diagram of an exemplary embodiment of a bio-material detecting apparatus.

FIG. 17 is another embodiment of a schematic block diagram of a bio-material detecting apparatus.

Referring to FIG. 17, the reflective type bio-materials detecting apparatus 500 according to the present embodiment includes a light source 501, that is part of an illuminating optical system, irradiating excitation light onto a reflective type bio-chip 550, a light diffusing device 502, a collimating lens 504, and a condensing lens 507. Moreover, the bio-material detecting apparatus 500 includes an excitation light absorbing filter 510, that is a part of a detecting optical system for detecting fluorescent light L' emitted from the bio-chip 550 due to the irradiated excitation light, a projection optical system 515, and a photodetector 518. In the present embodiment a beam splitter 505 for separating the excitation light L irradiated onto the bio-chip 550 and the fluorescent light L' emitted from the bio-chip 550 from each other, a mirror 513 folding an optical path, and a stage 520, on which the bio-chip 550 is mounted, are additionally included.

The light source 501, the light diffusing device 502, the collimating lens 504, and the condensing lens 507, the excitation absorbing filter 510, and the photodetector 518 are substantially the same as the corresponding components in the embodiment of a bio-materials detecting apparatus 400 shown in FIG. 16, and thus, detailed descriptions thereof are omitted here.

The beam splitter 505 is an optical member transmitting the excitation light L irradiated from the light source 501 to the bio-chip 550, and reflects the fluorescent light L' emitted from the bio-chip 550. Since the wavelength of the fluorescent light L' is longer than the excitation light L, in one embodiment a dichroic mirror may be used as the beam splitter 505. In one embodiment, the beam splitter 505 may be configured to transmit the wavelength of the fluorescent light L' emitted from the bio-chip 550 and reflect the other wavelengths. In such an embodiment, arrangements of the illuminating optical system and the detecting optical system may be changed. The dichroic mirror is an example of the beam splitter 505, and the present embodiment is not limited thereto. For example, alternative embodiments of the beam splitter 505 may separate the excitation light L and the fluorescent light L' using a polarization thereof. In such an alternative embodiment, the excitation light L irradiated from the light source 501 has a predetermined polarization, and the beam splitter 505 is transparent with respect to the polarization of the excitation light L. Since the fluorescent light L' emitted from the bio-chip 550 has no polarization, some polarization component will be reflected by the beam splitter 505.

The projection optical system 515 is an optical system for projecting the fluorescent light emitted from the bio-chip 550 to the photodetector 518, and is adjusted so that a spot of the fluorescent light may be formed exactly on the photodetector 518.

When the light spot of the excitation light L covers the entire surface of the bio-chip 550, the photodetector 518 may detect simultaneously all of the fluorescent images emitted from the bio-chip 550. When the light spot of the excitation light L covers only a part of the bio-chip 550, the stage 520 may move the bio-chip 550 so that the excitation light may cover the entire surface of the bio-chip 550 in a time-sequential manner. In addition, the photodetector 518 may obtain the fluorescent images of the entire area of the bio-chip 550 in a time-sequential order.

In the previous embodiments, the illuminating optical system or the projection optical system is a refractive optical system including lenses, however, the previous embodiments are not limited to the above example. For example, the optical systems in the above embodiments may be reflective optical systems including concave or convex mirrors as illustrated in FIGS. 5-12.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. A substrate for detecting samples, the substrate comprising:
    a body; and
    a plurality of micro lenses arranged on the body and configured for attachment to at least one sample,
    wherein the at least one sample emits fluorescent light, and
    wherein the plurality of micro lenses condense the fluorescent light emitted from the at least one sample via refraction.

2. The substrate of claim 1, wherein the body may be formed of a glass, a semiconductor, a dielectric material, a metal material, a polymer or a combination thereof.

3. The substrate of claim 1, wherein the plurality of micro lenses are formed of an inorganic material, an organic material, a dielectric material, a polymer or a combination thereof.

4. The substrate of claim 1, wherein surfaces of the plurality of micro lenses are surface treated so that the at least one sample may be attached to the surfaces of the micro lenses.

5. The substrate of claim 4, wherein the surfaces of the plurality of micro lenses are hydrophilic, and regions surrounding each of the plurality of micro lenses are hydrophobic.

6. The substrate of claim 1, wherein the body is formed of a hydrophobic material and the plurality of micro lenses are formed of a hydrophilic material.

7. The substrate of claim 1, wherein the plurality of micro lenses have at least one of convex, concave, and flat-hemispherical shapes.

8. The substrate of claim 1, further comprising:
    a plurality of anti-reflection layers formed on surfaces of the plurality of micro lenses to transmit the fluorescent light emitted from the at least one sample.

9. The substrate of claim 8, wherein the anti-reflection layers are hydrophilic.

10. The substrate of claim 1, further comprising:
    reflection layers disposed between the plurality of micro lenses and the body to reflect the fluorescent light emitted from the at least one sample.

11. The substrate of claim 1, further comprising:
    reflection layers disposed on surfaces of the plurality of micro lenses to reflect the fluorescent light emitted from the samples.

12. A method of fabricating a substrate of claim 1 for detecting samples, the method comprising:
    applying a photoresist on the substrate;
    patterning the photoresist to form patterns corresponding to the plurality of micro lenses;
    forming the plurality of micro lenses on the substrate using the patterned photoresist; and
    applying different materials to the plurality of micro lenses and a plurality of regions surrounding each of the plurality of micro lenses to adjust at least one of a hydrophilic property and a hydrophobic property of at least one of the plurality of micro lenses and the plurality of regions surrounding each of the plurality of micro lenses.

13. The method of claim 12, wherein the substrate may be formed of a glass, a semiconductor, a dielectric material, a metal material, a polymer or a combination thereof.

14. The method of claim 12, wherein the forming of the plurality of micro lenses comprises:
    reflowing the patterned photoresist to deform the patterned photoresist into the plurality of micro lenses.

15. The method of claim 14, wherein the substrate has a hydrophobic property and the photoresist has a hydrophilic property.

16. The method of claim 12, wherein the forming of the plurality of micro lenses comprises:
    reflowing the patterned photoresist to deform the patterned photoresist into the plurality of micro lenses; and
    etching an entire upper surface of the substrate, on which the deformed photoresist is formed, to form the plurality of micro lenses.

17. The method of claim 16, further comprising:
    surface treating the surfaces of the plurality of micro lenses to attach at least one sample to the plurality of micro lenses.

18. The method of claim 17, wherein the substrate has a hydrophobic property, and the surfaces of the plurality of micro lenses are treated to have hydrophilic properties.

19. The method of claim 12, wherein the patterning the photoresist comprises:
    forming a dielectric material layer on the substrate before applying the photoresist on the substrate,
    and the forming of the plurality of micro lenses comprises:
    reflowing the patterned photoresist to deform the patterned photoresist into the plurality of micro lenses; and
    etching an upper surface of the substrate, on which the deformed photoresist is formed, to form the plurality of micro lenses using the dielectric material layer.

20. The method of claim 19, wherein the substrate has a hydrophobic property and the dielectric material layer has a hydrophilic property.

21. A bio-material detecting apparatus comprising:
    a bio-chip comprising:
        at least one bio material which emits fluorescent light when excitation light is irradiated thereon; and
        a substrate according to claim 1; and
    a photodetector positioned where the fluorescent light is condensed and which detects the fluorescent light.

22. The bio-material detecting apparatus of claim 21, wherein the photodetector is disposed at a bottom surface side of the substrate, which is opposite to a surface where the plurality of micro lenses are arranged.

23. The bio-material detecting apparatus of claim 21, wherein the photodetector is disposed at a surface of the substrate on which the plurality of micro lenses are arranged.

24. The bio-material detecting apparatus of claim 21, wherein the photodetector is one of a photomultiplier tube, a charge coupled device, a complementary metal oxide semiconductor image sensor.

25. The bio-material detecting apparatus of claim 21, further comprising:
an excitation light absorption filter disposed between the bio-chip and the photodetector,
wherein the excitation light absorption filter transmits the fluorescent light and absorbs the excitation light.

26. A bio-material detecting apparatus comprising:
a substrate according to claim 1; wherein the plurality of micro lenses are disposed on a top surface of the substrate; and at least one bio material is disposed on the plurality of micro lenses, wherein the at least one bio material emits fluorescent light when excitation light is irradiated thereon;
and a photodetector disposed at a predetermined distance from the top surface of the substrate,
wherein the predetermined distance positions the photodetector a location wherein a cross sectional area of the fluorescent light emitted from the bio material and passed through at least one of the plurality of micro lenses is at a minimum.

27. The bio-material detecting apparatus of claim 26, wherein the substrate and the plurality of micro lenses are integrally formed as a single, unitary and indivisible member.

28. A bio-chip comprising:
a substrate on which a plurality of micro lenses are arranged; and
at least one bio-material which emits fluorescent light when excited by an excitation light, the at least one bio-material being disposed on the plurality of micro lenses,
wherein the plurality of micro lenses condense fluorescent light emitted from the at least one bio-material via refraction.

29. The bio-chip of claim 28, wherein surfaces of the plurality of micro lenses are surface treated so that the at least one bio-material may be attached to the surfaces of the micro lenses.

30. The bio-chip of claim 29, wherein the surfaces of the micro lenses have hydrophilic properties and regions on a surface of the substrate around the micro lenses have hydrophobic properties.

31. The bio-chip of claim 28, wherein the plurality of micro lenses are formed of a hydrophilic material and the body is formed of a hydrophobic material.

32. The bio-chip of claim 28, further comprising:
anti-reflection layers disposed on the surfaces of the plurality of micro lenses to transmit the fluorescent light.

33. The bio-chip of claim 28, further comprising:
reflection layers disposed between the plurality of micro lenses and the body to reflect the fluorescent light.

34. The bio-chip of claim 28, further comprising:
reflection layers disposed on surfaces of the plurality of micro lenses to reflect the fluorescent light.

35. The bio-chip of claim 28, further comprising:
a photodetector disposed on a surface of the substrate which is substantially opposite to a surface where the plurality of micro lenses are arranged, and the plurality of micro lenses condense the fluorescent light onto the photodetector.

36. The bio-chip of claim 35, wherein the photodetector and the substrate are integrally formed as a single, unitary and indivisible unit.

37. The bio-chip of claim 35, wherein the photodetector comprises a plurality of pixels and wherein the plurality of pixels correspond to the plurality of micro lenses in one of a one-to-one manner and a one-to-many manner.

38. The bio-chip of claim 35, further comprising:
an excitation light absorption filter disposed between the substrate and the photodetector,
wherein the excitation light absorption filter transmits the fluorescent light and absorbs the excitation light.

* * * * *